United States Patent
Meinel et al.

(10) Patent No.: US 11,206,824 B2
(45) Date of Patent: Dec. 28, 2021

(54) GAS DELIVERY DEVICE COMPRISING A GAS RELEASING MOLECULE AND A GAS PERMEABLE MEMBRANE

(71) Applicant: Julius-Maximilians-Universitaet Wuerzburg, Wuerzburg (DE)

(72) Inventors: Lorenz Meinel, Wuerzburg (DE); Christoph Steiger, Wuerzburg (DE); Christian Wunder, Eibelstadt (DE)

(73) Assignee: Julius-Maximilians-Universitaet Wuerzburg, Wuerzburg (DE)

( * ) Notice: Subject to any disclaimer, the term of this patent is extended or adjusted under 35 U.S.C. 154(b) by 359 days.

(21) Appl. No.: 15/542,100

(22) PCT Filed: Jan. 7, 2016

(86) PCT No.: PCT/EP2016/050146
§ 371 (c)(1),
(2) Date: Jul. 7, 2017

(87) PCT Pub. No.: WO2016/110517
PCT Pub. Date: Jul. 14, 2016

(65) Prior Publication Data
US 2018/0271086 A1 Sep. 27, 2018

(30) Foreign Application Priority Data
Jan. 8, 2015 (EP) .................................... 15150532

(51) Int. Cl.
*A61M 35/00* (2006.01)
*A01N 1/02* (2006.01)
(Continued)

(52) U.S. Cl.
CPC ......... *A01N 1/0226* (2013.01); *A01N 1/0236* (2013.01); *A01N 1/0242* (2013.01);
(Continued)

(58) Field of Classification Search
CPC .............................. A61F 13/00; A61M 35/30
See application file for complete search history.

(56) References Cited

U.S. PATENT DOCUMENTS 4,687,481 A * 8/1987 Nuwayser ............ A61K 9/7084
424/449
5,882,674 A 3/1999 Herrmann et al.
(Continued)

FOREIGN PATENT DOCUMENTS

WO WO 2009/133278 11/2009

OTHER PUBLICATIONS

Steiger et al. "Oral drug delivery of therapeutic gases—Carbon monoxide release for gastrointestinal diseases", 2014, Journal of Controlled Release, 189, pp. 46-53. (Year: 2014).*

*Primary Examiner* — Jonathan M Hurst
(74) *Attorney, Agent, or Firm* — Smith Patent, LLC; Chalin A. Smith

(57) ABSTRACT

The present invention relates to a gas delivery device comprising a gas releasing molecule and a gas permeable membrane. The invention also relates to the use of the gas delivery device for delivery of gas to an extracorporeal transplant, extracorporeal cells, a brain-dead transplant donor or foodstuff and in therapy. The invention further relates to the use of a gas permeable and liquid and solid impermeable membrane to separate a gas releasing molecule and its non-gaseous degradation products from an extracorporeal transplant, extracorporeal cells, a brain-dead transplant donor or foodstuff.

18 Claims, 9 Drawing Sheets

(51) Int. Cl.
*A61K 33/00* (2006.01)
*A61K 33/24* (2019.01)
*A61K 31/555* (2006.01)
*A61K 33/04* (2006.01)

(52) U.S. Cl.
CPC ............ *A61K 31/555* (2013.01); *A61K 33/00* (2013.01); *A61K 33/04* (2013.01); *A61K 33/24* (2013.01); *A61M 35/30* (2019.05)

(56) References Cited

U.S. PATENT DOCUMENTS

| | | | |
|---|---|---|---|
| 2003/0220623 A1* | 11/2003 | Sugiyama | A61F 13/493 604/378 |
| 2004/0241065 A1 | 12/2004 | Kampa et al. | |
| 2004/0260253 A1* | 12/2004 | Rosati | A61M 35/00 604/289 |
| 2008/0021373 A1* | 1/2008 | Rosati | A61M 37/0015 604/22 |
| 2008/0097282 A1* | 4/2008 | Hole | A61K 9/7007 604/23 |
| 2008/0206831 A1* | 8/2008 | Coffey | C12N 5/0068 435/176 |
| 2009/0202617 A1* | 8/2009 | Ward | A61K 9/1271 424/447 |
| 2011/0052650 A1 | 3/2011 | Morris et al. | |
| 2012/0003293 A1* | 1/2012 | Miller | A43B 17/003 424/445 |
| 2014/0221907 A1* | 8/2014 | Scholz | A61F 13/00051 604/25 |
| 2014/0230815 A1 | 8/2014 | Gribb et al. | |

* cited by examiner

GAS DELIVERY DEVICE COMPRISING A GAS RELEASING MOLECULE AND A GAS PERMEABLE MEMBRANE

PRIORITY

This application corresponds to the U.S. national phase of International Application No. PCT/EP2016/050146, filed Jan. 7, 2016, which, in turn, claims priority to European Patent Application No. 15.150532.8 filed Jan. 8, 2015, the contents of which are incorporated by reference herein in their entirety.

FIELD OF THE INVENTION

The present invention relates to a gas delivery device comprising a gas releasing molecule and a gas permeable membrane. The invention also relates to the use of the gas delivery device for delivery of gas to an extracorporeal transplant, extracorporeal cells, a brain-dead transplant donor or foodstuff and in therapy. The invention further relates to the use of a gas permeable and liquid and solid impermeable membrane to separate a gas releasing molecule and its non-gaseous degradation products from an extracorporeal transplant, extracorporeal cells, a brain-dead transplant donor or foodstuff.

BACKGROUND OF THE INVENTION

Gases such as carbon monoxide (CO), hydrogen sulfide ($H_2S$) and nitric oxide (NO) have been traditionally perceived as harmful gases. This perception is shifting, e.g. towards deploying gases for attenuating ischemia-reperfusion injury in organ transplants, for therapeutic purposes or for meat treatment to increase consumer perception.

Transplants are harvested from the dead after a death certificate has been issued. Until either the transplant team is at the site of the body for organ harvest or the organ is taken from a specialized team the bodies are kept alive. Upon retrieval, the organ is perfused (removal of blood) with a special nutrient solution. Thereafter, the organ is typically stored in a bag with a known and defined amount of a nutrient solution and this bag is closed. The closed bag is placed into another bag, holding ice. Importantly, the amount of nutrition solution is standardized such that the volume is sufficient to prevent freezing during intended duration of transport. University of Wisconsin (UW) solution is currently the most popular static cold solution for abdominal organ preservation (R. F. Parsons et al., Current opinion in organ transplantation, 19 (2014) 100-107). Previous studies, however, showed, that e.g. 18-hours of cold ischemic time for liver grafts in normal UW solution resulted in hepatic injury (T. Kaizu et al., American journal of physiology. Gastrointestinal and liver physiology, 294 (2008) G236-244). It was also reported that cold preservation for 24 hours in normal UW solution is associated with approximately 70% mortality after LTX (T. Kaizu et al., Hepatology, 43 (2006) 464-473).

Preservation of rat liver grafts in UW solution containing 5% CO (CO-UW solution) for 18 to 24 hours reduced neutrophil extravasation, down-regulated the hepatic mRNA for tumor necrosis factor alpha and intercellular cell adhesion molecule 1, reduced hepatic extracellular signal-regulated kinase activation and ameliorated SEC damage and hepatic I/R injury after LTX in rodents (A. Ikeda et al, official publication of the American Association for the Study of Liver Diseases and the International Liver Transplantation Society, 15 (2009) 1458-1468). Pre-treatment of donors with inhaled CO ameliorates liver transplantation associated I/R injury with increased hepatic HSP70 expression, particularly in the Kupffer cell (macrophage in the liver) population (L. Y. Lee et al, official publication of the American Association for the Study of Liver Diseases and the International Liver Transplantation Society, 17 (2011) 1457-1466). Effects of inhaled carbon monoxide, nitric oxide and hydrogen sulfide on ischemia-reperfusion injury in organ transplantation are e.g. further summarized by Siriussawakul et al. (J Transplant: 819382, 819388 pp. (2012)).

WO 03/000114 also suggests administering CO to a transplant donor, to the organ to be transplanted in situ in the donor before transplanting, to the organ ex vivo, and/or the recipient of the organ before, during or after transplantation. It is further suggested to administer CO to a donor of whom cells are obtained for transplantation, to the obtained cells ex vivo and/or to the recipient of the cell transplant. It is described that organs, tissues or isolated cells may be exposed to an atmosphere comprising carbon monoxide gas, to a liquid carbon monoxide composition, e.g., a liquid perfusate, storage solution, or wash solution having carbon monoxide dissolved therein, or both. To form an atmosphere that includes carbon monoxide gas inside a chamber or space it is described to provide a vessel containing a pressurized gas comprising carbon monoxide gas, and releasing the pressurized gas from the vessel into the chamber or space. The gases can also be released into an apparatus that culminates in a breathing mask or breathing tube. Liquid CO compositions are described to be obtainable by exposing a liquid to a continuous flow of carbon monoxide. CO can also be "bubbled" directly into the liquid. Furthermore, a liquid may be passed through tubing that allows gas exchange where the tube runs through an atmosphere comprising CO.

However, the described equipment needed for providing gas to form an atmosphere comprising the gas of interest or a liquid comprising the gas is impractical.

WO 04/045598 describes a different approach for delivering CO to an extracorporeal or isolated organ for avoiding post-ischemic damage by contacting the organ with a composition including a metal carbonyl compound. Thereby, CO is described to be made available by dissociation of the metal carbonyl present in the composition in dissolved form, by release of CO upon contact of the metal carbonyl compound with a solvent or a tissue, or on irradiation. Pizarro e.g. described that storing a rodent liver 48 h in cold ischemia, with an isolated normothermic perfused liver system (INPL) in modified University of Wisconsin (UW) solution, with 50 µM tricarbonylchloro ruthenium-glycinato (CORM-3), improved the perfusion flow, the intrahepatic resistance and the metabolic capacity (M. D. Pizarro et la, Cryobiology, 58 (2009) 248-255). Rabbit kidneys flushed with Celsior solution supplemented with CO-RMs (50 µM) and stored at 4° C. for 24 h displayed at reperfusion after TX a significantly higher perfusion flow rate (PFR), glomerular filtration rate, and sodium and glucose reabsorption rates compared to control kidneys (A. Sandouka et al., Kidney international, 69 (2006) 239-247). CO delivered through CORM-2 i.v. administration (20 mg/kgBW) in mice almost completely protects against lethal renal warm ischemia reperfusion injury through prevention of HMGB1 nuclear-cytoplasmic translocation and release (Y. Ruan et al., Kidney international, 86 (2014) 525-537). CORM-3 supplementation in standard University of Wisconsin solution (1 ml, 100 µmol/L) for 26 h of cold preservation of rodent kidney grafts has a significant impact on decreasing cellular and graft injury, and improving survival through its anti-apoptotic effects (A. Sener et al., The Journal of urology, 190 (2013) 772-778).

However, a current problem associated with the use of gas releasing molecules, such as CORMs, is the potential toxicity of these molecules. Pizarro et al. (Cryobiology, 58 (2009) 248-255) e.g. raised the question of toxicity of the ruthenium containing backbone of CORMs as they observed marked injury of liver stored in a solution containing inactive CORM3 (iCORM3). WO 2013/127380 also describes that pharmacological innocuousness of CO releasing molecules is not yet satisfyingly solved.

There is thus still a lack of a non-toxic and simple device for gas delivery to e.g. extracorporeal transplants, extracorporeal cells, a brain-dead transplant donor or foodstuff. With respect to transplants, it is particularly advantageous if the device allows for a long time between donation and transplantation to the recipient thus e.g. enabling an increase of the distance the transplant can be shipped. The device should also be easy to use and to prepare. It is further advantageous, if the device allows for long storage, e.g. in an ambulance.

SUMMARY OF THE INVENTION

The present invention overcomes the above mentioned problems by providing a gas delivery device (also just referred to as "device" in the following) comprising a first chamber enclosed by gas-, liquid- and solid-tight first chamber walls, wherein at least a part of the first chamber walls is replaced by a first gas permeable and liquid and solid impermeable membrane, wherein the first chamber comprises a gas releasing molecule or an electrochemical gas generator.

The device thus allows for release of gas from the inside of the first chamber to the outside of the device through the first gas permeable, but liquid and solid impermeable membrane. Non-gaseous substances comprised inside the first chamber are retained therein. The gas delivery device of the present invention is, e.g., for delivery of gas to an extracorporeal transplant, extracorporeal cells, a brain-dead transplant donor or foodstuff.

DETAILED DESCRIPTION OF THE PREFERRED EMBODIMENTS

Gas can, e.g., be delivered by the gas releasing device into a solution used for storing a transplant, when the gas delivery device is immersed therein, while the solution (and the transplant stored in the solution) does not get in contact with liquid or solid substances comprised in the first chamber of the device. This is important, as thereby the organ during transport (or after harvest and during perfusion to remove the blood (right after harvest)) may be exposed to gases alone. Exposure of the organ to the gas releasing molecule or its degradation products comprised in the first chamber of the gas releasing device is prevented. For these reasons, toxicity concerns related to the gas releasing molecules and further non-gaseous compounds comprised in the first chamber of the gas releasing device can be mitigated and safety and efficacy assessments may be focused on gas alone. The device of the present invention may thus comprise a gas releasing molecule, which is toxic. Such gas releasing molecule (or its non-gaseous degradation products) would have detrimental effects e.g. on a transplant when coming into contact therewith.

Figure 3A:
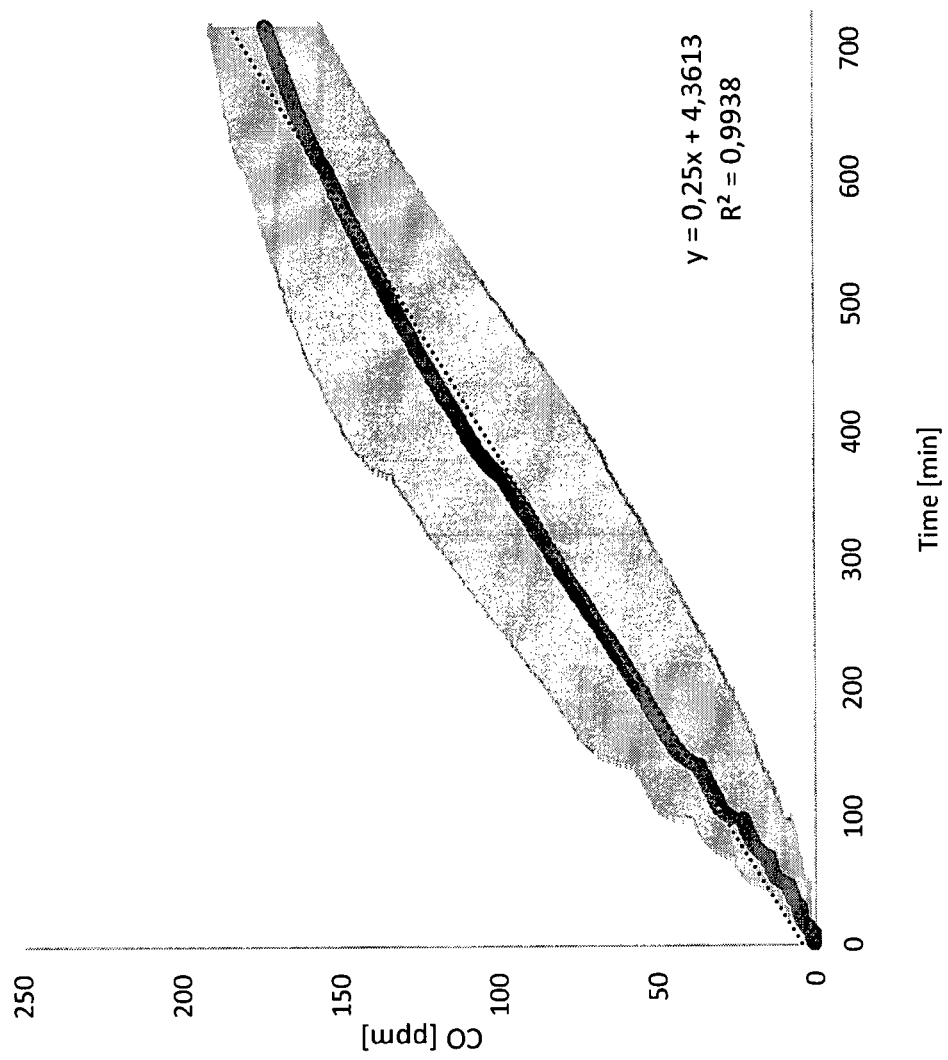
FIG. 3a is a graphic representation of the CO release pattern of a one PTFE membrane based device immersed in 450 ml water (n=3, ±SD).
Figure 3B:
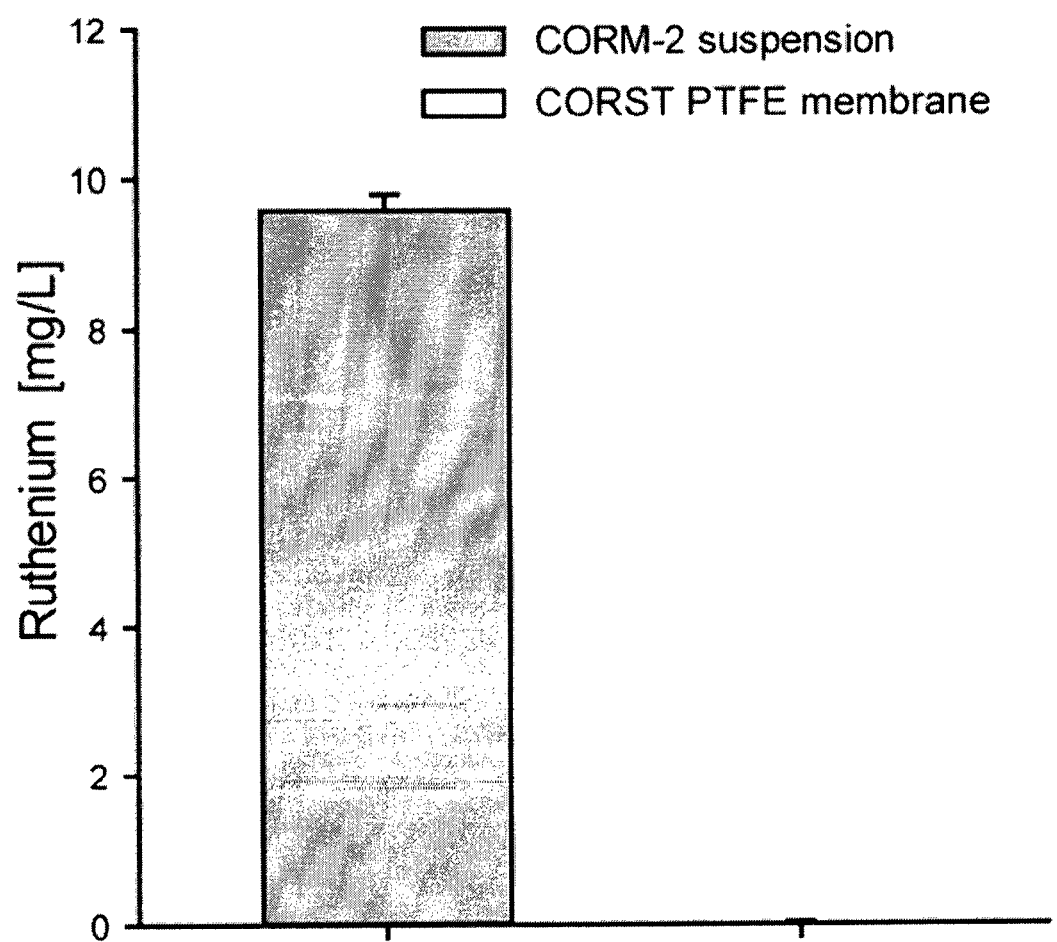
FIG. 3b is a graphic representation of the measured ruthenium content of medium (450 ml water) to which 12 mg of a CORM-2 and 150 mg $Na_2SO_3$ was added in comparison to medium into which the device with one PTFE membrane was immersed for 12 hours, the device containing 12 mg CORM-2, 6 mg $Na_2SO_3$ and 4 ml of water (n=3, ±SD).
Figure 5:
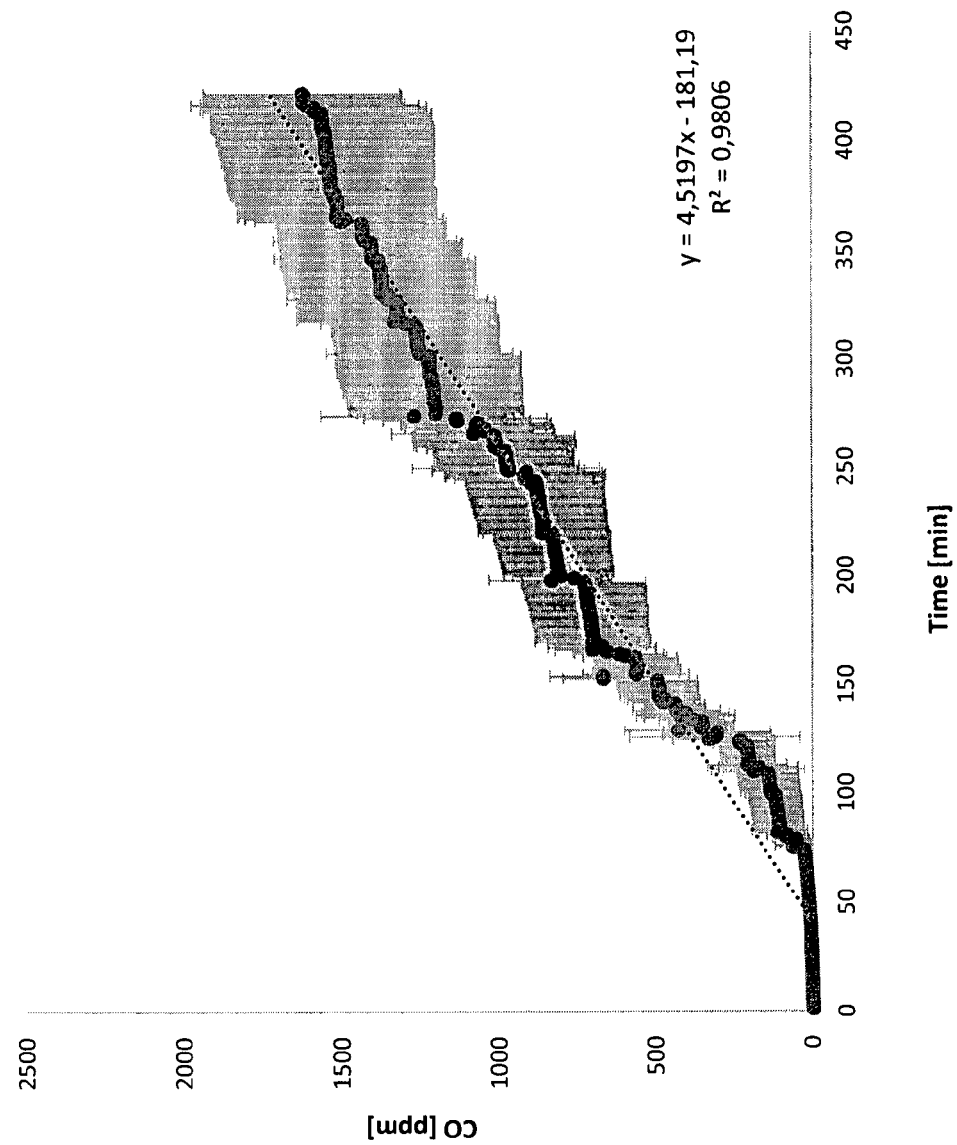
FIG. 5 is a graphic representation of the CO release pattern of a two silicone membranes based device immersed in 600 ml water (n=3, ±SD).

In this respect it is also referred to e.g. FIGS. 3a, 3b, 5 showing a constant release of CO from a gas delivery device according to the present invention comprising CORM-2 (tricarbonyldichlororuthenium(II) dimer; $Ru(CO)_3Cl_2$) (FIGS. 3a and 5) while no toxic ruthenium was detected in the solution, in which the gas delivery device of the present invention was immersed (FIG. 3b).

In one embodiment, the gas delivery device of the present invention comprises a second chamber enclosed in part by the first gas permeable and liquid and solid impermeable membrane and for the remaining part by gas-, liquid- and solid-tight second chamber walls and optionally by part of the first chamber walls, wherein at least a part of the second chamber walls is replaced by a second gas permeable and liquid and solid impermeable membrane. In one embodiment, the enclosure of the second chamber is formed by a part of the first gas permeable and liquid and solid impermeable membrane, the gas-, liquid- and solid-tight second chamber walls and optionally by part of the first chamber walls.

The first and/or second gas permeable and liquid and solid impermeable membrane (also just referred to as first and second "gas permeable membrane" or simply "membrane") preferably comprises one or more of the following materials of the groups consisting of polytetrafluoroethylene (PTFE, Teflon), butyl rubber, cellulose acetate, ceramic, dimethyl silicone rubber 60, ethyl cellulose, fluorosilicone, Kel F, Latex, methyl cellulose, metal organic framework membranes (see e.g. Chem. Soc. Rev., 2014, 43, 6116-6140), mylar, natural rubber, nitrile silicone, nylon, polycarbonate, polyethersulfone, polyethylene, polypropylene, polystyrene, polyvinylalcohol, polyvinyl chloride, polyvinylidene fluoride, vinylidene chloride-vinyl chloride and zeolith.

In a preferred embodiment, the first membrane comprises polytetrafluoroethylene (PTFE). In another embodiment, the first gas membrane comprises silicone.

In one embodiment of the present invention the first chamber walls of the device of the present invention essentially consist of the gas permeable and liquid and solid impermeable membrane. In this case, the first chamber walls (gas-, liquid- and solid-tight) are replaced in their entirety by the gas permeable and liquid and solid impermeable membrane. The first chamber walls (where not replaced by the first gas permeable membrane) consist of a tight material (impermeable for gas, liquid and solid), such as e.g. stainless steel. Preferably, in the device of the present invention the first membrane has a surface for gas release of 0.2-20 cm$^2$, more preferably 2-10 cm$^2$ or 1-5 cm$^2$. The surface proportion of the first membrane to tight first chamber walls can, e.g., be 0.01-0.95, 0.05-0.6 or 0.1-0.3.

Preferably, the gas releasing molecule in the present invention is a CO, H$_2$S or NO releasing molecule. In one embodiment of the present invention, the gas releasing molecule is a metal organic compound. In one embodiment, the gas releasing molecule has a molecular weight of 1000 g/mol or less. It can also have a molecular weight of 700 g/mol or less or 450 g/mol or less.

Most preferably, the gas releasing molecule is a CO releasing molecule (CORM) and the CO releasing molecule is a metal carbonyl compound. The metal carbonyl compound comprises e.g. a complex of an element of the group of Rh, Ti, Os, Cr, Mn, Fe, Co, Mo, Ru, W, Re, Ir, B and C. More preferably, the metal carbonyl compound comprises a complex of an element of the group of Rh, Mo, Mn, Fe, Ru, B and C, even more preferably of the group of Rh, Fe, Mn, Mo, B and C. The metal carbonyl compounds may be regarded as complexes, because they comprise CO groups coordinated to a metal centre. However, the metal may be bonded to other groups by other than coordination bonds, e.g. by ionic or covalent bonds. Thus, groups other than CO, which form part of the metal carbonyl compound, need not strictly be "ligands" in the sense of being coordinated to a metal centre via a lone electron pair, but are referred to herein as "ligands" for ease of reference.

Thus, the ligands to the metal may all be carbonyl ligands. Alternatively, the carbonyl compound may comprise at least one ligand which is not CO. Ligands which are not CO are typically neutral or anionic ligands, such as halide, or derived from Lewis bases and having N, P, O or S or a conjugated carbon group as the coordinating atom(s). Preferred coordinating atoms are N, O and S. Examples include, but are not limited to, sulfoxides such as dimethylsulfoxide, natural and synthetic amino acids and their salts for example, glycine, cysteine, and proline, amines such as NEt$_3$ and H$_2$NCH$_2$CH$_2$NH$_2$, aromatic bases and their analogues, for example, bi-2,2'-pyridyl, indole, pyrimidine and cytidine, pyrroles such as biliverdin and bilirubin, drug molecules such as YC-1 (2-(5'-hydroxymethyl-2'-furyl)-1-benzylindazole), thiols and thiolates such as EtSH and PhSH, chloride, bromide and iodide, carboxylates such as formate, acetate, and oxalate, ethers such as Et$_2$O and tetrahydrofuran, alcohols such as EtOH, and nitriles such as MeCN. Other possible ligands are conjugated carbon groups, such as dienes, e.g. cyclopentadiene (C$_5$H$_5$) or substituted cyclopentadiene. The substituent group in substituted cyclopentadiene may be for example an alkanol, an ether or an ester, e.g. —(CH$_2$)$_n$OH where n is 1 to 4, particularly —CH$_2$OH, —(CH$_2$)$_n$OR where n is 1 to 4 and R is hydrocarbon preferably alkyl of 1 to 4 carbon atoms and —(CH$_2$)$_n$OOCR where n is 1 to 4 and R is hydrocarbon preferably alkyl of 1 to 4 carbon atoms. The preferred metal in such a cyclopentadiene or substituted cyclopentadiene carbonyl complex is Fe.

Preferably, Mo(CO)$_3$(CNC(CH$_3$)$_2$COOH)$_3$ CORM-ALF794, CORM-1, CORM-2, CORM-3, or CORM-401 is used as gas releasing molecule in the present invention.

It is also explicitly referred to WO 2008/130261 and US20070219120 A1 for a description of CO releasing molecules. There aldehydes according to formula I

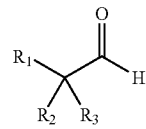

formula I are disclosed which can also be used as gas releasing molecule in the present invention wherein R$_1$, R$_2$ and R$_3$ are each independently selected from alkyl, substituted alkyl, cycloalkyl, substituted cycloalkyl, heterocyclyl, substituted heterocyclyl, alkylheterocyclyl, substituted alkylheterocyclyl, alkenyl, substituted alkenyl, aryl, substituted aryl, heteroaryl, substituted heteroaryl, alkylaryl, substituted alkylaryl, wherein the number of C atoms is 1-12 or 1-6 in each case hydroxy, alkoxy, amino, alkylamino, mercapto, alkylmercapto, aryloxy, substituted aryloxy, heteroaryloxy, substituted heteroaryloxy, alkoxycarbonyl, acyl, acyloxy, acylamino, alkylsulfonyl, alkylsulfinyl, F, Cl, Br, NO$_2$ and cyano; or two or more of R$_1$, R$_2$ and R$_3$ are taken together to form a substituted or unsubstituted carbocyclic or heterocyclic ring structure or an derivative thereof. For any substituent the number of C atoms is 1-12 or 1-6.

A derivative of a compound of formula I being an acetal, hemiacetal, aminocarbinol, aminal, imine, enaminone, imidate, amidine, iminium salt, sodium bissulfite adduct, hemimercaptal, dithioacetal, 1,3-dioxepane, 1,3-dioxane, 1,3-dioxalane, 1,3-dioxetane, α-hydroxy-1,3-dioxepane, α-hydroxy-1,3-dioxane, α-hydroxy-1,3-dioxalane, α-keto-1,3-dioxepane, α-keto-1,3-dioxane, α-keto-1,3-dioxalane, α-keto-1,3-dioxetane, macrocyclic ester/imine, macrocyclic ester/hemiacetal, oxazolidine, tetrahydro-1,3-oxazine, oxazolidinone, tetrahydro-oxazinone, 1,3,4-oxadiazine, thiazolidine, tetrahydro-1,3-thiazine, thiazolidinone, tetrahydro-1,3-thiazinone, imidazolidine, hexahydro-1,3-pyrimidine, imidazolidinone, tetrahydro-1,3-pyrimidinone, oxime, hydrazone, carbazone, thiocarbazone, semicarbazone, semithiocarbazone, acyloxyalkyl ester derivative, O-acyloxyalkyl derivative, N-acyloxyalkyl derivative, N-Mannich base derivative or N-hydroxymethyl derivative can also be used as gas releasing molecule in the present invention.

The gas releasing molecule in the present invention can e.g. also be trimethylacetaldehyde, 2,2-dimethyl-4-pentenal, 4-ethyl-4-formyl-hexanenitrile, 3-hydroxy-2,2-dimethylpropanal, 2-formyl-2-methyl-propylmethanoate, 2-ethyl-2-methyl-propionaldehyde, 2,2-dimethyl-3-(p-methylphenyl)propanal or 2-methyl-2-phenyl propionaldehyde.

In one embodiment an oxalate, an oxalate ester or amide is used as gas releasing molecule comprised in the device of the present invention.

In one embodiment, carboxyborane, a carboxyborane ester or a carboxyborane amide is used as gas releasing molecule in the present invention. Such gas releasing molecules are particularly described in WO 2005/013691. In one embodiment of the present invention

is thus used as gas releasing molecule wherein x is 1, 2 or 3, y is 1, 2 or 3, z is 0, 1 or 2, x+y+z=4, each Q is O$^-$, representing a carboxylate anionic form, or is OH, OR, NH$_2$, NHR, NR$_2$, SR or halogen, where the or each R is alkyl (preferably of 1 to 4 carbon atoms), each Z is halogen, NH$_2$, NHR', NR'$_2$, SR' or OR' where the or each R' is alkyl (preferably of 1 to 4 carbon atoms). More preferably, z is 1 and/or y is 1 and/or x is 3. In one embodiment, at least one Q is O$^-$ or OR and the composition includes at least one metal cation, wherein the metal cation is preferably an alkali metal cation or an earth metal cation.

When a boronocarboxylate is used as gas releasing molecule it is most preferably Na$_2$(H$_3$BCO$_2$), also known as CORM-A1.

In one embodiment of the present invention, a metal organic framework loaded with a therapeutic gas is used as gas releasing molecule. Metal-organic frameworks (MOFs) are coordination polymers with an inorganic-organic hybrid frame comprising metal ions and organic ligands coordinated with the metal ions. In one embodiment, the gas releasing molecule is a MOF loaded with at least one Lewis base gas chosen from the group comprising of NO, CO and H$_2$S, such as MIL-88B-FE or NH$_2$-MIL-88B-Fe. In another embodiment the gas releasing molecule comprised in the device of the present invention is a MOF loaded with at least one Lewis base gas chosen from the group comprising NO, CO and H$_2$S as described in WO2009/133278 A1, particularly as described in claims 1 to 13 therein to which it is explicitly referred.

As H$_2$S releasing molecule a sulfide, disulfide or a polysulfide can be used. For example, NaHS and Na$_2$S are H$_2$S releasing molecules particularly usable in the present invention. GYY 4137 (CAS 106740-09-4) is another H$_2$S releasing molecule usable in the present invention.

NO releasing molecules are e.g. diazeniumdiolates. Non-diazeniumdiolate forms of NO donors including S-nitroso compounds and C-nitroso compounds may also be used. NO-releasing imidates, thioimidates, methanetrisdiazeniumdiolate, and a bisdiazeniumdiolate derived from 1,4-benzoquinone dioxime can e.g. also be used.

In one embodiment, the gas releasing molecule releases gas upon contact with a gas release triggering compound (trigger compound). Contact thus means that a reaction between the gas releasing molecule and the trigger compound can take place which results into gas release.

In one embodiment the gas delivery device of the present invention has a tightly (impermeable to gas, liquid and solid) sealable opening in the walls of the first chamber. A trigger compound can thus be filled into the first chamber through the sealable opening shortly before the device is used for gas delivery to e.g. an extracorporeal transplant, extracorporeal cells, a brain-dead transplant donor or foodstuff. The opening is then tightly sealed. Upon contact with the trigger compound the gas releasing molecule starts to release substantial amounts of gas. The device is thus "activated" and gas can be delivered through the gas permeable membrane to an extracorporeal transplant, extracorporeal cells, a brain-dead transplant donor or foodstuff, but any liquid or solid is retained in the first chamber of the device to avoid contact thereof with the extracorporeal transplant, extracorporeal cells, a brain-dead transplant donor or foodstuff. The device of the present invention is thus very versatile, as e.g. the trigger compound and its amount can be chosen depending on which gas release profile from the device is desired.

Preferably, the gas delivery device of the present invention is one which comprises a trigger compound in the first chamber of the device.

The trigger compound can e.g. be a sulfur-containing compound or a nitrogen-containing compound, an oxidating compound, an acid or a base or water.

When the gas releasing molecules is a metal carbonyl compound, the trigger compound is preferably a carbonyl substituting ligand, such as a sulfur-containing compound or a nitrogen-containing compound. The sulfur containing compound can e.g. be selected from an alkali metal or alkaline-earth metal salt, preferably a sodium salt, of sulfite, dithionite, or metabisulfite, or a compound bearing at least one thiol moiety, such as cysteine or glutathione.

Examples of oxidating compounds to be used as trigger compound in the present invention are peroxides, perborates, percarbonates, and nitrates of which calciumperoxide, di benzoyl peroxide, hydrogenperoxide urea, sodium perborate, sodium percarbonate and silver nitrate are preferred. As acid, e.g. HCl can be used. In one embodiment, the trigger compound is a non-enzymatic compound. Preferably, the trigger compound is a compound with a molecular weight of less than 10.000 g/mol, more preferably of less than 7000 g/mol or even less than 1000 g/mol. The trigger compound can, e.g., also be water or a solvent. A preferred gas releasing molecule which releases gas upon contact with water is ALF186.

For a metal carbonyl compound as gas releasing molecule and a sulfur containing compound or other electron withdrawing compound as the trigger compound it is e.g. believed that, when this trigger compound comes into contact with the metal carbonyl compound, a ligand substitution takes place thereby triggering gas release.

When the gas releasing molecule is sodium sulfide, an acid, such as HCl, can e.g. be used as trigger compound to trigger gas release (H$_2$S) from the gas releasing molecule (sodium sulfide).

When the gas releasing molecule is an S-nitroso compound, a Copper ion, such as in Copper(II) sulfate and copper(I) chloride can be used to trigger gas release (NO) from the gas releasing molecule (Singh, R. J., et al., Journal of Biological Chemistry 271(31) (1996): 18596-18603).

In one embodiment of the device of the present invention, the device comprises a trigger compound in the first chamber, wherein the trigger compound is selected from the group consisting of a sulfur containing compound, a nitrogen containing compound, an oxidating compound, and water. This is particularly the case, when the gas releasing molecule is a metal carbonyl compound. In one embodiment, the device of the present invention comprises in the first chamber (in addition to the gas releasing molecule) water or another liquid and a trigger compound, such as e.g. one of the following compounds: a sulfur containing compound, a nitrogen containing compound or an oxidating compound. Even when the gas releasing molecule does not release substantial amounts of gas upon contact with the liquid, such as water, itself, the liquid can help to bring the gas releasing molecule into contact with the trigger compound so that a gas releasing reaction can take place between them.

Of course, one or more trigger compounds can be comprised in the first chamber of the device of the present invention.

In one embodiment, the device of the present invention comprises a trigger compound in the first chamber, wherein the first chamber is separated into at least two compartments, one compartment comprising the gas releasing molecule and another compartment comprising the trigger compound. Separation can, e.g., be by at least one inner membrane splitting the first chamber into separate compartments. The separation helps to avoid a premature release of the gas from the gas releasing molecule and thus from the gas delivery device when both, the gas releasing molecule and the trigger compound are comprised in the first chamber. The device can be activated by breaking the inner membrane(s) (e.g. by vigorous shaking of the device or, by bending the inner membrane(s) until break; in the latter case the inner membrane(s) is/are designed to break before the remaining device is destroyed when the whole device is bended as the device must retains its function to allow only gas release, but no liquid or solid release).

Figure 9:
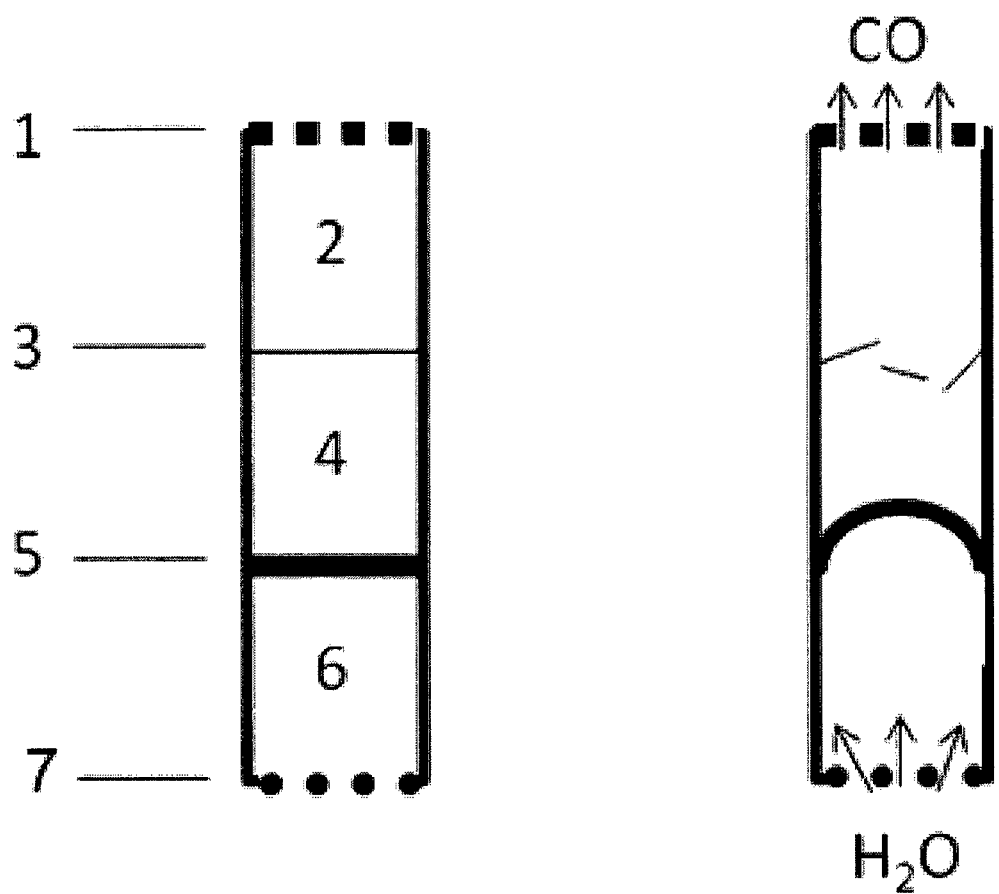
FIG. 9 is a schematic view of one embodiment of a device according to the invention.

Referring to the drawing of FIG. 9, in one embodiment, the device of the present invention is a device comprising a trigger compound and/or water in the first chamber, wherein the first chamber is separated into at least two compartments (2, 4) by an inner membrane (3), one compartment (2) comprising the gas releasing molecule and another compartment (4) comprising the trigger compound and/or water, the device further comprising an osmagent chamber (6) adjacent to at least one compartment (4) of the first chamber and enclosed by a part of the first chamber walls (5), which is flexible, and by part of semipermeable osmagent chamber walls (7), this osmagent chamber comprising an osmagent. The semipermeable osmagent chamber wall (7) is water permeable but solid impermeable. In one embodiment it is also impermeable to the osmagent in dissolved form. The osmagent chamber (6) is preferably adjacent to the compartment comprising the trigger compound and/or water. The osmagent may be any material that increases the osmotic pressure of the osmagent chamber (6). The osmagent chamber (6) must have an effective osmotic pressure greater than that of the surrounding aqueous medium wherein the device of the present invention is used, e.g. the nutrition medium in which an extracorporeal transplant is kept for storage so that there is a net driving force for water to enter the osmagent chamber. The osmotic pressure within the osmagent chamber (6) allows the hydrostatic pressure in the osmagent chamber (6) to increase such that pressure is exercised on the flexible part of the first chamber walls (5) and thereby bending into the adjacent compartment (4) of the first chamber. Thereby, pressure in the adjacent compartment (4) increases and is particularly also exerted on the inner membrane (3) which breaks by the increased pressure while the remaining walls of the first chamber are more stable and do not break. Thereby, contact between the gas releasing molecule and the trigger compound and/or water in the first chamber can take place which results into gas release from the device through the gas permeable and liquid and solid impermeable membrane (1).

The osmagent can be either soluble or swellable. Examples of osmotically effective solutes are inorganic and organic salts and sugars. Osmotically effective compounds that may be used herein include magnesium, calcium, sodium, potassium or lithium sulfate, magnesium, calcium, sodium, potassium or lithium chloride, sodium carbonate, sodium sulfite, calcium carbonate, potassium acid phosphate, calcium lactate, d-mannitol, urea, inositol, magnesium succinate, tartaric acid, water soluble acids, alcohols, surfactants, and carbohydrates such as sugars (e.g., raffinose, sucrose, glucose, lactose, fructose), sugar derivatives, algin, sodium alginate, potassium alginate, carrageenan, fucoridan, furcellaran, laminaran, hypnea, gum arabic, gum ghatti, gum karaya, locust bean gum, pectin and starch.

In one embodiment, the device of the present invention comprising a trigger compound in the first chamber is one wherein the gas releasing molecule is comprised in the first chamber as coated gas releasing molecule particles (particles "A" or A-particles) and/or the trigger compound is comprised in the first chamber as coated trigger compound particles (particles "B" or B-particles). A-particles do not comprise the trigger compound and B-particles do not comprise the gas releasing molecule, but of course, either particles may comprise other excipients. Contact of A particles with B particles is thus prevented by the coating around the A and/or B particles. The device is then e.g. activated by addition of a solvent to the first chamber through a tightly sealable opening in the walls of the first chamber to dissolve the coating(s). Contact between the gas releasing molecule and the trigger compound then induces gas release from the gas releasing molecule.

In one embodiment, the device of the present invention comprises a gas releasing molecule which releases gas upon irradiation. The walls of the device can be penetrable by irradiation. This e.g. allows for photo-activation of a gas releasing molecule such as a Photo-CORM from the outside when the Photo-CORM is comprised in the device. It is also possible that a source of irradiation is comprised in the device itself. E.g., the device may comprise an LED for release of gas from a gas releasing molecule upon irradiation by the LED. In one embodiment, the device of the present invention comprises a Photo-CORM and an LED in the first chamber. The LED is protected in the first chamber of the gas delivery device of the present invention from any contact with e.g. a nutrition medium in which an extracorporeal transplant is kept for storage. Photo-CORMs which can e.g. be comprised in the device of the present invention are CORM-1, $Fe(CO)_5$, the compound of

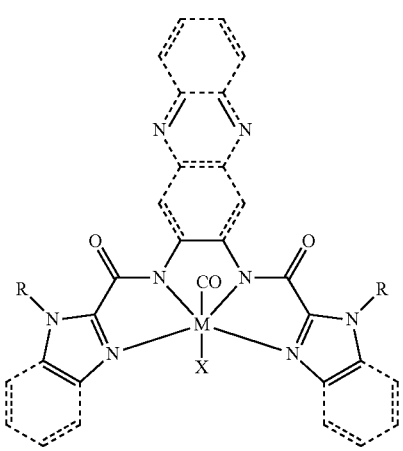

formula II wherein M is Fe(II) or Ru(II) and X is an O-donor such as $H_2O$, an N-donor, such as pyridine, or a P-donor such as $PPh_3$, and the dashed parts are present or not, the compound of

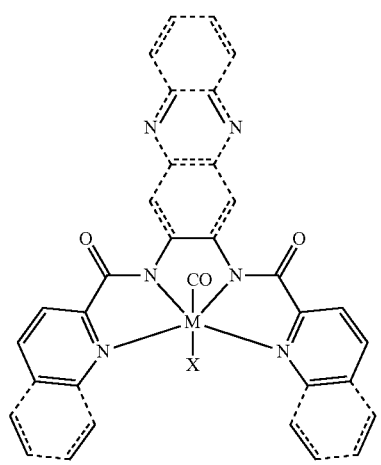

formula III wherein M and X are defined as in formula II above and the dashed parts are present or not, V(CO)$_6$, Mo(CO)$_6$, Mn(CO)$_5$ Cl Mn(CO)$_5$Br, Fe$_2$(CO)$_9$, Fe$_3$(CO)$_{12}$, Fe(CO)$_4$X$_2$ wherein X is Cl, Br, I, Co$_2$(CO)$_8$, Co(CO)$_4$I, Re$_2$(CO)$_{10}$, Ru(CO)$_4$, Mn(CO)$_3$(tpm)]PF$_6$ (tpm=tris(1-pyrazolyl)methane)), cis-[Fe(CO)$_2$(H$_2$NCH$_2$CH$_2$S)$_2$], (CORM-S1) or [Mn(CO)$_3$(tpm)]+. A gas releasing molecule gas release of which is increased by heat is e.g. CORM-A1.

In one embodiment, the device of the present invention comprises an electrochemical gas generator in the first chamber. Such gas generator may comprise an electrolyte containing a mesoxalic acid or a mesoxalate, a cathode formed of a noble metal, a mixture of noble metals or a material containing carbon, said cathode being in direct contact with said electrolyte, an anode formed of a noble metal, a mixture of noble metals or a material containing carbon, said anode being in direct contact with said electrolyte, and a control unit acting as a power source, said control unit being connected to said anode and said cathode. The device allows for gas release from the first chamber to the outside of the device through the gas permeable, but liquid and solid impermeable membrane. As the entire electrochemical gas generator is comprised in the first chamber of the present device, contact of e.g. a nutrition medium in which an extracorporeal transplant is kept for storage with unsterile or non-sterilizable parts of the electrochemical gas generator or parts of the gas generator which are incompatible with the nutrition medium (such as e.g. the power source) is prevented.

The gas delivery device of the present invention is preferably used for delivery of gas to an extracorporeal transplant, extracorporeal cells, a brain-dead transplant donor or foodstuff (such as meat). It is also possible to use the device for delivery of gas to an organ which is in a body, but isolated from the blood supply. The device of the present invention can e.g. be used for reduction or prevention of apoptosis or necrosis in a donor organ (transplant) during harvest, during perfusion or during transport. The gas delivery device of the present invention is also used in therapy and particularly for increasing the survival time of a transplant in a patient.

More preferably, the gas delivery device of the present invention is used for delivery of gas to an extracorporeal transplant, such as an extracorporeal liver transplant, extracorporeal kidney transplant, extracorporeal heart transplant or extracorporeal lung transplant, preferably an extracorporeal liver transplant.

The present invention also relates to the use of a gas permeable and liquid and solid impermeable membrane to separate a gas releasing compound and its non-gaseous degradation products from an extracorporeal transplant, extracorporeal cells, a brain-dead transplant donor or foodstuff.

For use, the gas delivery device can e.g. simply be placed into the nutrition medium in which the extracorporeal transplant is kept for storage. Gas (e.g. CO) is thus delivered by the device into the medium and thus to the transplant. The gas releasing device can also be placed into the body (such as the stomach) of the brain-dead transplant donor. Gas (e.g. CO) is generated by the gas releasing device in relevant amounts and throughout the time the body (not the brain) is kept alive. One may restrict the exposure of the body to the gas releasing device only after the death certificate has been issued. In another embodiment, the gas releasing device (e.g. having the form of a capsule, or a hollow tubing or any other geometry) can be placed into the main aorta such that e.g. CO is readily released into the perfusion fluid and in adjacent tissue parts of the respective organ. With the described methods, the gas can readily diffuse into the parenchymal or other tissues or interstitial or other fluids within the respective organ transplant.

Furthermore, the device can also be used to deliver gas to a severed limb. A device of the present invention comprising a trigger compound in the first chamber upon contact with which the gas releasing molecule release gas can, e.g., be immersed in a fluid, such as water, into which also the severed limb is immersed.

Further use of the device of the present invention can be made for delivery of gas, such as CO, to foodstuff, in particular meat. Treatment of meat with CO is known to increase consumer perception by providing a fresh, red color to the respective nutrition, as has recently been shown for mortadella (A. D. Pereira et al., Meat Sci. 97:164-173 (2014). CO treatment is established in the food industry, including the pretreatment of meat before packaging, or the exposure to CO saturated solutions during shipment. The device of the present invention can thus be used for gas delivery to meat for e.g. keeping the meat fresh upon harvest or during transport and storage.

The device of the present invention can also be used for delivery of gas to a sensor for sensor calibration. The sensor can thus be exposed to defined amounts of gas. Contact of the sensor with liquid or solid is prevented (even when the sensor is difficult to access) as any liquid or solid comprised in the first chamber of the device of the present invention is retained therein.

The amount of gas to be released by the device in a given time is easily tunable e.g. by the choice and amount of gas releasing molecule, by using a non-compressed or pre-compressed gas releasing molecule, by the choice and amount of the trigger compound, by the gas permeable membrane, the size of the gas permeable membrane and the use of a second gas permeable membrane. It is preferred that the first (and optionally also the second) gas permeable and liquid and solid impermeable membrane of the gas delivery device is exchangeable in the device of the present invention. This renders the gas delivery device even more versatile.

In one embodiment, the device of the present invention can comprise a compound as a "push component" in the first chamber, e.g. sodium hydrogen carbonate. From the push component a gas (such as $CO_2$ from sodium hydrogen carbonate) is released e.g. upon contact with water (when water is also comprised in the first chamber of the device). Due to the increase of pressure inside of the first chamber which builds up by the push component, overall gas release from the gas releasing device can be increased.

In one embodiment, the therapeutic device of the present invention releases between 0.1 1000 µmol gas (such as CO, $H_2S$ or NO) per h, preferably between 10 and 30 µmol gas (such as CO, $H_2S$ or NO) per h. In one embodiment, gas (such as CO, $H_2S$ or NO) is released from the device for at least 5, 10, 24 or 36 hours.

In a preferred embodiment, the device according to the present invention is a device as shown in the examples of this application.

The following examples are illustrative without restricting the scope of protection.

EXAMPLES

Amperometric Detection in the Headspace of the Storage Box

Figure 1:
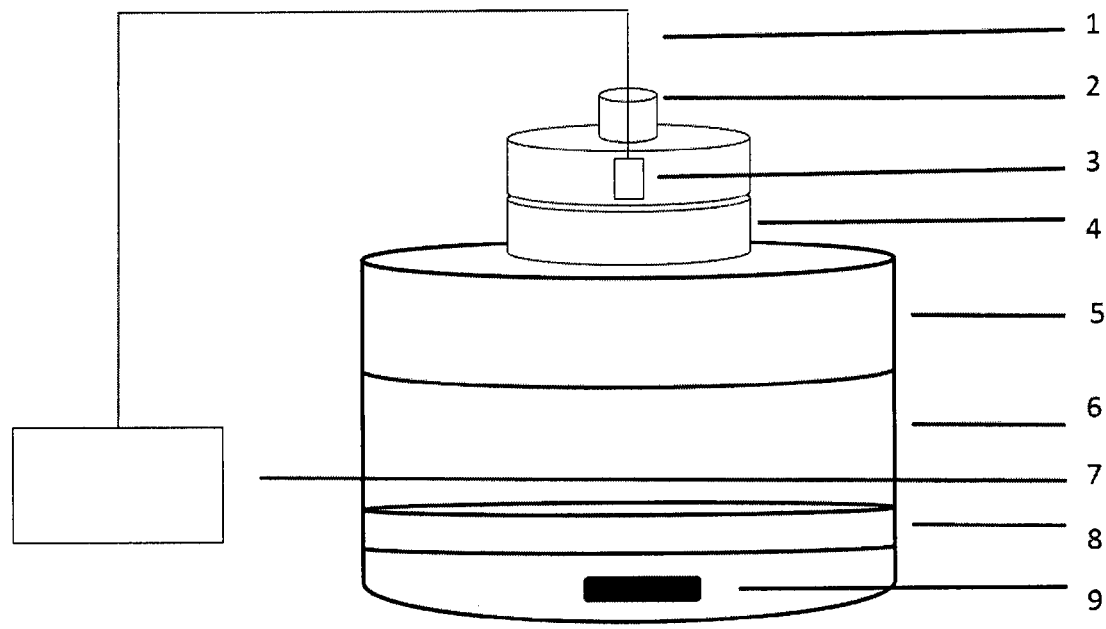
FIG. 1 depicts an amperometric CO detection system in accordance with the present invention that includes: 1. Cable; 2. Guide tube with glued in cable; 3. XXS CO LC sensor; 4. Flange; 5. Desiccator lid; 6. Desiccator; 7. X-am 5000; 8. Tile; and 9. Stirring bar.

The amperometric detection was performed as previously described [1] with modification. We used a desiccator (DN 100) (6) from DURAN Group GmbH (Wertheim/Main, Germany) as a model storage box for organs which was closed with a dessicator lid (5) (FIG. 1). For headspace CO detection a glassblower attached the lid (5) having an opening to a flange (DN 40) (4) from Gebr. Rettberg (Göttingen; Germany) which was sealed with a three-point flange clamp (Gebr. Rettberg, Göttingen, Germany) to another flange equipped with an XXS CO LC sensor (Draeger, Luebeck, Germany) (3) (App. 1). The sensor was connected to an X-am 5000 CO detector (Draeger, Luebeck, Germany) (7). The used cable (1) was glued into a guide tube (2) using a hot meld adhesive "Pattex Heißklebesticks" (Henkel AG & Co. KGaA, Düsseldorf, Germany). In a modification of the system the lid (5) was closed with a perforated plastic stopper instead of attaching the flange (4) to the lid (App. 2). The cable (1) connecting the sensor (3) for headspace CO detection to the detector (7) outside of the desiccator was glued in the plastic stopper with hot melt adhesive "Pattex Heißklebesticks" (Henkel AG & Co. KGaA, Düsseldorf, Germany). The dessicator can partially be filled with water, which is stirred by a stirring bar (9). A gas releasing device can be placed on the tile (8) so that it is immersed in the water without interfering with the stirring bar. The setup of the storage box (App. 1) is shown in FIG. 1.

ICP-OES Analytics:

Ruthenium content of the CO releasing device (also termed CO releasing system, CORST) surrounding medium was measured by inductively coupled plasma optical emission spectrometry (ICP-OES) with triple measurement of each data point at 240.3 nm, 245.6 nm, 245.7 nm, and 267.9 nm (ICP-OES Vista Pro Radial, Agilent Technologies, Santa Clara, Calif.). The result was referenced to a 10 mg/L ruthenium standard.

Materials:

Carbon monoxide releasing molecule 2 (CORM-2); (tricarbonyldichlororuthenium(II) dimer; [$Ru(CO)_3Cl_2$]) was purchased from Sigma Aldrich Chemie (Schnelldorf, Germany). Citric acid was from Jäkle Chemie (Nürnberg, Germany). $Na_2SO_3$ was purchased from Grüssing (Filsum, Germany). All other reagents were from Sigma Aldrich (Schnelldorf, Germany) and at least of pharmaceutical grade unless otherwise noted.

Example 1: One Membrane Based CO Release Device

Figure 2:
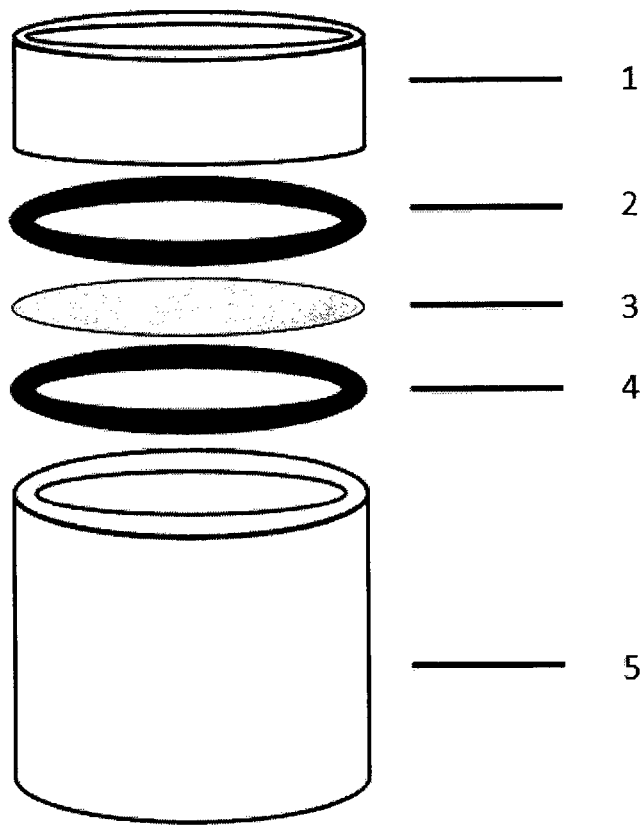
FIG. 2 depicts a gas delivery device in accordance with the present invention that includes: 1. Stainless steel lid; 2. Gasket ring (Ø 2 cm); 3. PTFE membrane (Ø 2 cm); 4. Gasket ring (Ø 2 cm); 5. Stainless steel reaction space.

A gas releasing device with a reaction space (5) and a lid (1) were machined from a stainless steel cylinder (Gebr. Reinhard GmbH & Co. KG, Würzburg, Germany) by the engineering tool shop of our department. For gas release the reaction space (approximate volume 4.5 ml) has one, the lid two open sites (FIG. 2). The CO release from the reaction space is controlled by one PTFE membrane (3) which is clamped between lid and reaction space. The membrane was dismantled with a nipper from a "Transducer Protector L" filter (Fresenius Medical Care Deutschland GmbH, Schweinfurt, Germany). The membrane is sealed towards the steel part by two gasket rings (20×2 mm, Schwarz GmbH, Würzburg, Germany) (2,4). The reaction space and the lid are pressed together with a flange clamp (Varian, Palo Alto, Calif.) sealing the device (not shown in FIG. 2) Therefore the vicinal apertures of lid and reactions space are shaped conically in the form of a flange.

12 mg CORM-2 and 6 mg $Na_2SO_3$ were weighted into the reaction space ((5) in FIG. 2). 4 ml water were added. The device was enclosed using a flange clamp. The desiccator (App.1) was filled with 450 ml water stirred at 600 rpm (Variomag Telesystem, Thermo Scientific, MA). The gas releasing device was immersed into the water in the desiccator. The desiccator was enclosed. CO measurement was performed in the headspace of the storage box (desiccator).

Equipped with one PTFE membrane of "Transducer Protector L" filters from Fresenius the device releases 0.25 ppm CO per minute with a zero order kinetic for at least 12 hours (FIG. 3a)

After immersion of the device in 450 ml medium for 12 hours, the medium (water) in the desiccator is not contaminated with ruthenium (<0.00 mg/L), as analysed by ICP-OES (FIG. 3b), nor by sulfite as analysed by the compendial method for iodometric determination [2]. The device thus enables a complete separation of the released therapeutic CO and degradation products of CORM-2 and $Na_2SO_3$ being retained in the reaction space of the gas releasing device.

Example 2: Two Silicone Membranes Based CO Release Device

Figure 4:
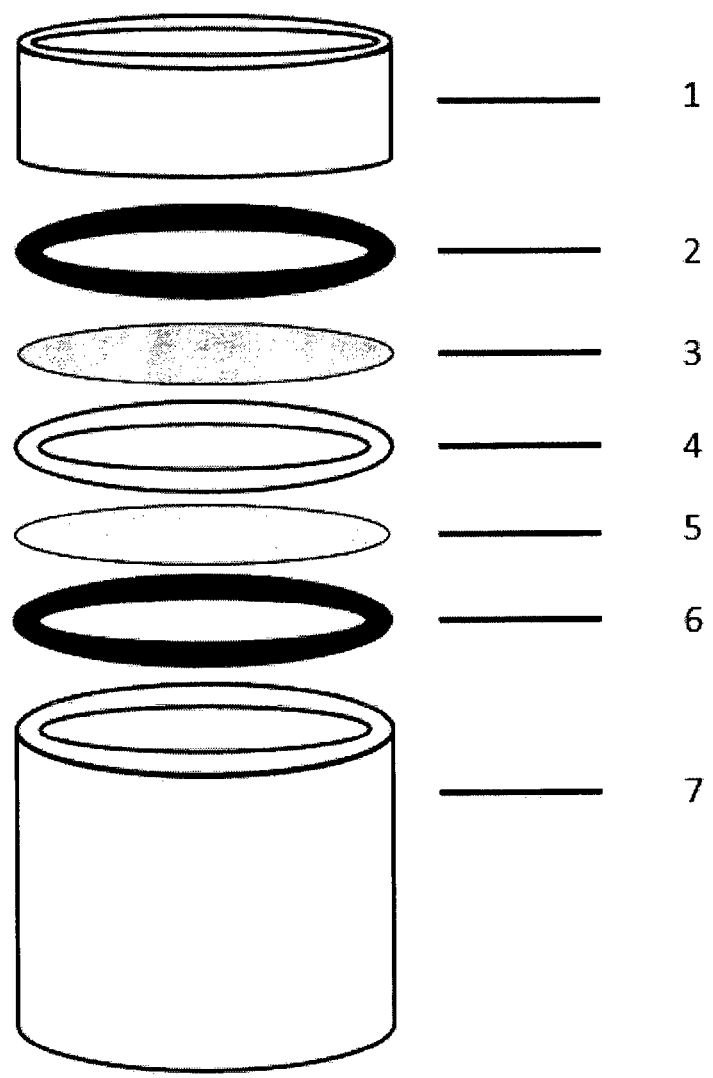
FIG. 4 depicts a gas delivery device in accordance with the present invention that includes: 1. Stainless steel lid; 2. Gasket ring (Ø 2 cm); 3. silicone membrane (Ø 2 cm) 4. Teflon lining disc (Ø 2 cm); 5. silicone membrane (Ø 2 cm); 6. Gasket ring (Ø 2 cm); 7. Stainless steel reaction space.

A gas releasing device with a reaction space (7) and a lid (1) were machined from a stainless steel cylinder (Gebr. Reinhard GmbH & Co. KG, Würzburg, Germany) by the engineering tool shop of our department. For gas release the reaction space (approximate volume: 4.5 ml) has one, the lid two open sites (FIG. 4). The CO release from the reaction space is controlled by two SSP-M823 0.01" silicone membranes from SSP (New York, USA) (3,5) which are clamped between lid and reaction space. The membranes are sealed towards the steel part by two gasket rings (20×2 mm, Schwarz GmbH, Würzburg, Germany) (2,6). A two mm thick PTFE ring (Schwarz GmbH, Würzburg, Germany) (4) separates the membranes and creates a gas phase between the reaction space and the outer transplant solution throughout the release process. The reaction space and the lid are pressed together with a flange clamp (Varian, Palo Alto, Calif.) sealing the device (not shown in FIG. 4). Therefore the vicinal apertures of lid and reactions space are shaped conically in the form of a flange.

30 mg CORM-2, 16 mg Na$_2$SO$_3$, 7 mg citric acid, and 13 mg trisodiumcitrate were weighted into the reaction space. ((7) in FIG. 4). 3.0 ml water were added. The device was enclosed using a flange clamp. The desiccator (App. 2) was filled with 600 ml water stirred at 600 rpm (Variomag Telesystem, Thermo Scientific, MA). The gas releasing device was immersed into the water in the desiccator. The desiccator was enclosed. CO measurement was performed in the headspace of the storage box (desiccator).

Equipped with two SSP-M823 0.01" silicone membranes from SSP the device releases 4.5 ppm CO per minute with a zero order kinetic for at least 7 hours (FIG. 5).

After immersion of the device in 600 ml medium for 12 hours, the medium (water) is not contaminated with ruthenium (<0.00 mg/L), as analysed by ICP-OES, nor by sulfite as analysed by the compendial method for iodometric determination [2]. The device thus enables a complete separation of the released therapeutic CO and degradation products of CORM-2 and Na$_2$SO$_3$ being retained in the reaction space of the gas releasing device.

Example 3: Two Silicone Membranes Based H$_2$S Release Device

The setup was adopted from example 2. 1 mL of a 0.7 mg/mL sodium sulfide solution was injected to the reaction space ((7) in FIG. 4). A 250 µL Eppendorf vial without lid was filled with 100 µL 0.1M HCL and also transferred to the reaction space in upright position. In this setting we applied two SSP-M823 0.01" silicone membranes from SSP (New York, USA) and used App. 1 filled with 600 ml water stirred at 600 rpm (Variomag Telesystem, Thermo Scientific, MA). Before transferring the device to App. 1 the compounds were mixed by shaking the device manually.

Figure 6:
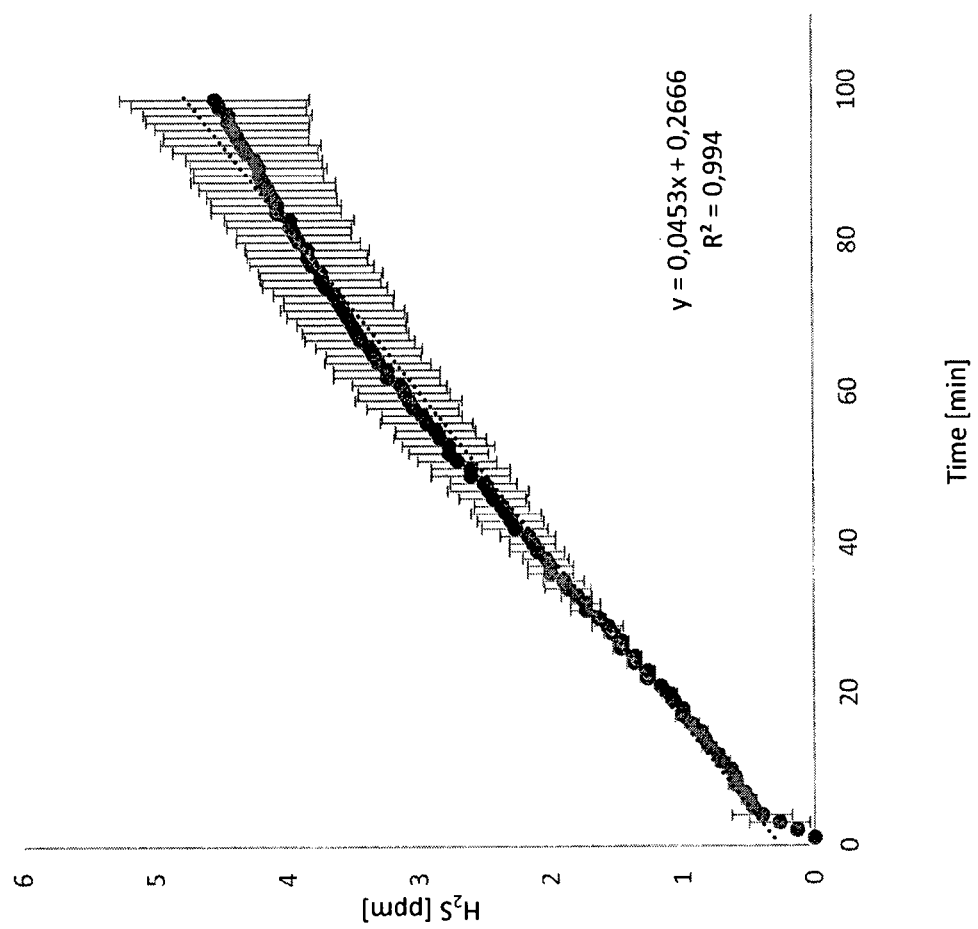
FIG. 6 is a graphic representation of the $H_2S$ release pattern of a two silicone membranes based device immersed in 600 ml water (n=3).

Equipped with two SSP-M823 0.01" silicone membranes the device releases 0.04 ppm H$_2$S per minute with a zero order kinetic for at least 3 hours (FIG. 6).

Example 4: Tunable Two Silicone Membranes Based CO Release Device

The setup was adopted from example 2. Two experiments were conducted in a first set of experiments. In each case 12 mg CORM-2 and 6 mg Na$_2$SO$_3$ were weighted into the reaction space of the gas releasing device. The reaction was started with 3.0 ml water. In this setting we applied either two SSP-M823 0.01", or two 0.04" silicone membranes from SSP (New York, USA) and used App. 1 filled with 600 ml water stirred at 600 rpm (Variomag Telesystem, Thermo Scientific, MA)

Figure 7:
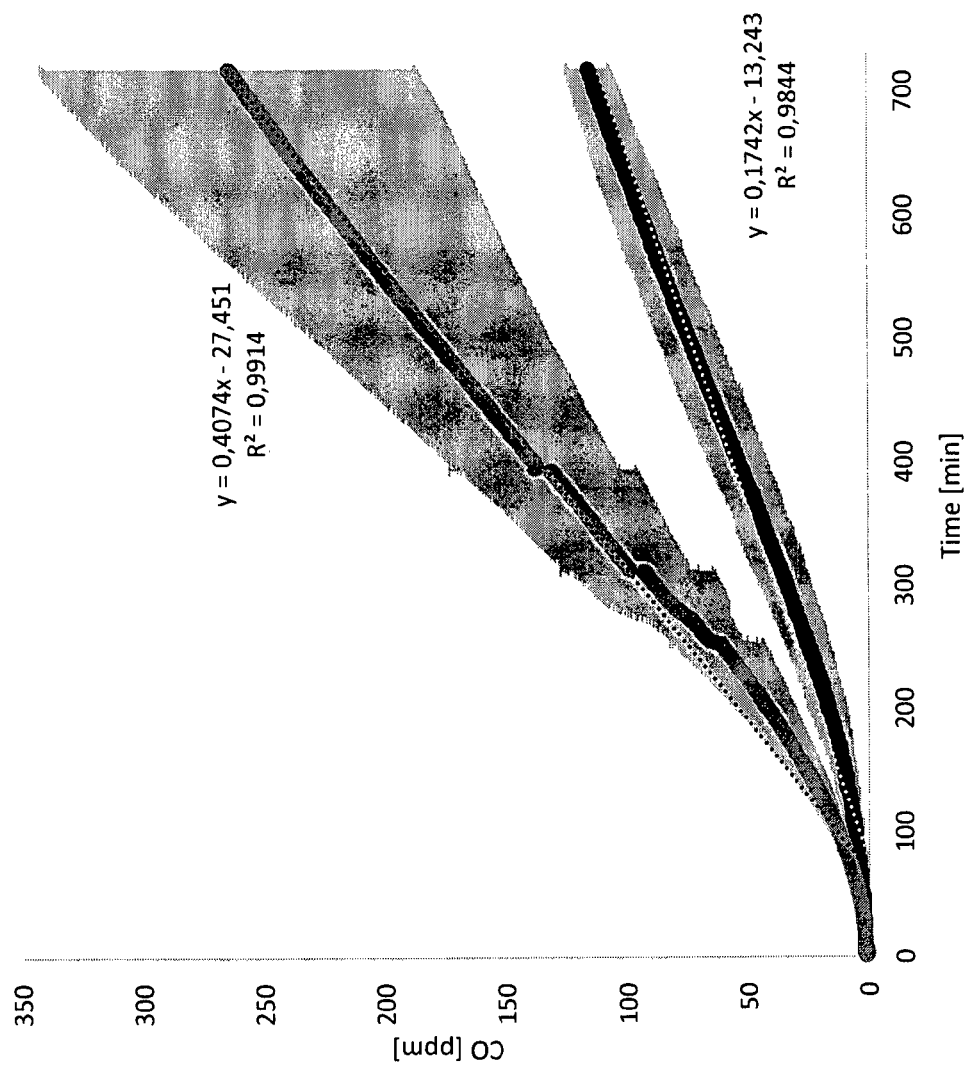
FIG. 7 is a graphic representation of the CO release pattern of a two silicone membranes (0.01" silicone (grey pattern) or 0.04" silicone (black pattern)) based device immersed in 600 ml water (n=3, ±SD).

Equipped with 0.01" silicone membranes the device releases 0.4 ppm CO per minute with a zero order kinetic for at least 12 hours. When the membranes are, however, replaced with 0.04" silicone membranes the device releases 0.17 ppm CO per minute (FIG. 7).

In a second set of experiments a tablet containing 12 mg CORM-2 was put into the reaction space of the gas releasing device (equipped with two 0.01" silicone membranes) or 12 mg CORM-2 (as is, i.e. not pre-compressed into a tablet) and 6 mg Na$_2$SO$_3$ were weighted into the reaction space of the gas releasing device. The reaction was started with 3.0 ml water. In this setting we applied two SSP-M823 0.01" membranes from SSP (New York, USA) and used App. 1 filled with 600 ml water stirred at 600 rpm (Variomag Telesystem, Thermo Scientific, MA).

The tablet (called OCORS tablet) 12 mm Ø was prepared as follows: Na$_2$SO$_3$ crystals of appropriate size were collected using an AS 200 Retsch analytical sieve tower (Haan, Germany) and the 250-500 µm fraction was collected. These crystals were coated using a solution consisting of 8.6 g Eudragit E PO, 0.9 g sodium dodecyl sulfate, 1.3 g stearic acid, 4.3 g talcum, 50 mL of distilled water and 50 mL of absolute ethanol. The dye Sam specracol erythrosine Ik was added in minute amounts. The preparation was homogenized for 20 min at 13,000 rpm using a Silent Crusher M (Heidolph, Schwabach, Germany) and sieved through a mesh with 375 µm aperture size for removal of disruptive agglomerates. 60 g Na$_2$SO$_3$ crystals were coated with a Mini-Coater (Glatt, Binzen, Germany) used in top-spray configuration at a temperature of 45° C., an atomizing pressure of 0.86 bar. The coating solution was pumped into the coater by a Flocon 1003 flexible tube pump (Roto-Consulta, Lucerne, Switzerland) at 0.7 mL/min. Coating lasted for about 2 hours and the fluidized bed was maintained for another 10 minutes, thereafter. Tablets were prepared from a blend of 72 mg pulverized citric acid*H$_2$O, 128 mg pulverized trisodium citrate*2H$_2$O, 200 mg coated Na$_2$SO$_3$ (vide supra), 41.4 mg CORM-2 and 1.54 g tableting mixture (consisting of lactose, cellulose, aluminium oxide and magnesium stearate; from Meggle, Wasserburg am Inn, Germany), prepared for 30 minutes in a Turbula T2F mixer (WAB AG, Muttenz, Switzerland). The resulting blend was transferred into an eccentric press tableting machine model FE136SRC from Korsch (Berlin, Germany) using a 12 mm tablet punch from Korsch (Berlin, Germany) resulting in average tablets weights as of 580 mg. A tablet coating solution was prepared from 0.9 g PEG 400 as pore former in 100 mL acetone into which 5.8 g cellulose acetate was slowly added under stirring at 130 rpm. The tablet cores were completely immersed into the coating solution and following removal air dried using an air gun at about 60° C. for 1 min. Thereafter, the pre-dried sample was transferred into a desiccation and left in a ED 53 drying chamber from Binder (Tuttlingen, Germany) at 50° C. for 30 min. Tablet cores were coated 10 times (also see [1]).

Figure 8:
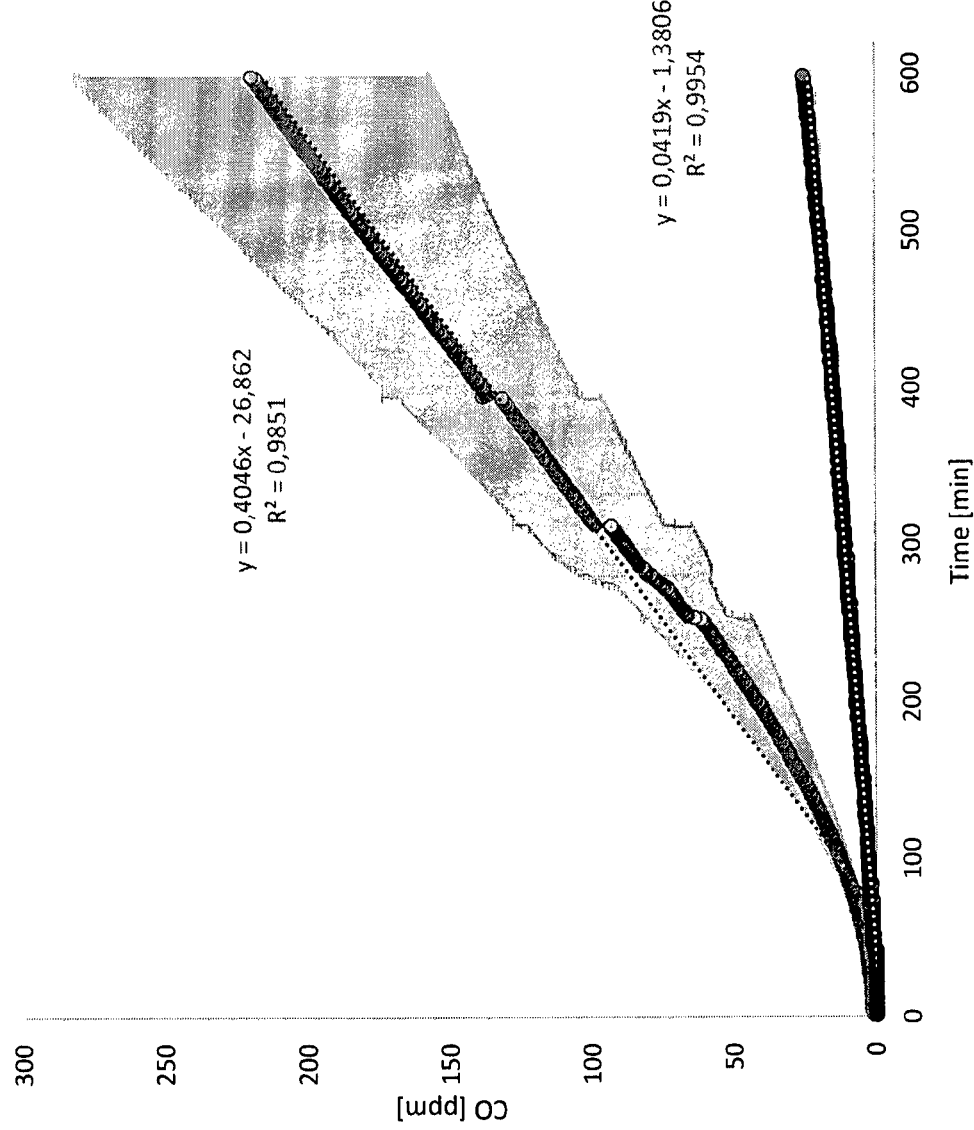
FIG. 8 is a graphic representation of the CO release pattern of a two 0.01" silicone membranes based device immersed in 600 ml water (n=3, ±SD). Sulfite triggered CO release from 12 mg of a "pure" CORM-2 (grey pattern) or OCORS with 12 mg CORM-2 (black pattern) membranes. CO release was controlled by the kinetic of the CO source (OCORS tablet or "pure" CORM-2).

CO release per time from the device with the OCORS tablet was one tenth compared to the release of CO from the device containing the CORM-2, which was not pre-compressed (FIG. 8).

[1] C. Steiger, T. Luhmann, L. Meinel, Oral drug delivery of therapeutic gases—carbon monoxide release for gastrointestinal diseases, Journal of controlled release: official journal of the Controlled Release Society, 189 (2014) 46-53.

[2] p. Natrii sulfis anhydricus—Pharmacopoea Europaea 6.0 (2008).

The invention claimed is:

1. A gas delivery device comprising a first chamber enclosed by gas-, liquid- and solid-tight first chamber walls, wherein:
   (a) at least a part of the first chamber walls is replaced by a first gas permeable and liquid and solid impermeable silicone membrane, wherein said first silicone membrane is a polydimethylsiloxane membrane,
   (b) said first silicone membrane includes a surface for gas release that ranges in size from 0.2 cm$^2$ to 20 cm$^2$,
   (c) the proportion of a surface area defined by said surface for gas release of said first silicone membrane to a surface area defined by said remaining first chamber walls ranges from 0.01 to 0.95, and
   (d) the first chamber comprises a gas releasing molecule selected from the group consisting of a carbon monoxide releasing molecule (CORM), a hydrogen sulfide (H$_2$S) releasing molecule and a nitric oxide (NO)

releasing molecule, further wherein said gas releasing molecule is a metal organic compound, wherein the metal is selected from the group consisting of Mo, Ru, and B.

2. The gas delivery device according to claim 1, wherein the device comprises a second chamber enclosed in part by the first gas permeable and liquid and solid impermeable membrane and for the remaining part by gas-, liquid- and solid-tight second chamber walls, and optionally by part of the first chamber walls, wherein at least a part of the second chamber walls is replaced by a second gas permeable and liquid and solid impermeable membrane.

3. The gas delivery device according to claim 1, wherein said metal organic compound is loaded with at least one Lewis base gas selected from the group consisting of NO, CO and $H_2S$.

4. The gas delivery device according to claim 1, wherein said gas releasing molecule is a carbon monoxide releasing molecule (CORM) and the CORM is a metal carbonyl compound comprised of CO groups coordinated to a metal centre, further wherein said metal centre is an element selected from the group consisting of Mo, Ru, and B.

5. The gas delivery device according to claim 1, wherein the device further comprises a gas release triggering compound in the first chamber.

6. The gas delivery device according to claim 5, wherein the gas release triggering compound is selected from the group consisting of a sulfur containing compound, a nitrogen containing compound, an oxidating compound, and water.

7. The gas delivery device according to claim 5, wherein the first chamber is separated into at least two compartments, wherein one compartment comprises the gas releasing molecule and another compartment comprises the gas release triggering compound.

8. The gas delivery device according to claim 5, wherein the gas releasing molecule is present in the first chamber as coated gas releasing molecule particles and/or the gas release triggering compound is present in the first chamber as coated gas release triggering particles.

9. The gas delivery device according to claim 4, wherein the gas releasing molecule is a selected from the group consisting of $Mo(CO)_3(CNCH_2COOH)_3$, CORM-ALF794, CORM-1, CORM-2, CORM-3, CORM-401 and CORM-A1.

10. The gas delivery device according to claim 1, wherein said surface for gas release of said first silicone membrane ranges from 2 $cm^2$ to 10 $cm^2$.

11. The gas delivery device according to claim 1, wherein said surface for gas release of said first silicone membrane ranges from 1 $cm^2$ to 5 $cm^2$.

12. The gas delivery device according to claim 1, wherein the proportion of the surface area defined by said surface for gas release of said first silicone membrane to the surface area defined by said remaining first chamber walls ranges from 0.05 to 0.6.

13. The gas delivery device according to claim 1, wherein the proportion of the surface area defined by said surface for gas release of said first silicone membrane to the surface area defined by said remaining first chamber walls ranges from 0.1 to 0.3.

14. A method of delivering gas to an extracorporeal transplant, extracorporeal cells, a brain-dead transplant donor or foodstuff using the gas delivery device according to claim 1.

15. The method according to claim 14, wherein gas is delivered to an extracorporeal transplant.

16. The method according to claim 14, wherein said gas delivery device is used in therapy.

17. The method according to claim 14, wherein said gas delivery device increases the survival time of a transplant in a patient.

18. A method of separating a gas releasing compound and its non-gaseous degradation products from an extracorporeal transplant, extracorporeal cells, a brain-dead transplant donor or foodstuff using the gas delivery device according to claim 1.

* * * * *